United States Patent [19]

Cromer

[11] Patent Number: 5,082,009
[45] Date of Patent: Jan. 21, 1992

[54] HAND-HELD FOOT CALLUS REMOVER

[76] Inventor: Marsha J. Cromer, 17th ASG-CM Box 2264, APO San Francisco, Calif. 96504

[21] Appl. No.: 398,943

[22] Filed: Aug. 28, 1989

[51] Int. Cl.⁵ ............................................. A45D 29/18
[52] U.S. Cl. ..................................... 132/76.4; 132/73
[58] Field of Search .................... 132/73, 73.5, 76.4; 51/150, 328, 394, 407; 606/131, 160; 433/142

[56] References Cited

U.S. PATENT DOCUMENTS

| | | | |
|---|---|---|---|
| 217,300 | 7/1879 | Starr | 51/407 |
| 894,161 | 7/1908 | Miller | 132/76.4 |
| 1,370,753 | 3/1921 | Loring | 132/76.4 |
| 2,434,407 | 1/1948 | Hope | 51/391 |
| 2,479,514 | 8/1949 | Rucker | 132/76.4 |
| 2,495,370 | 1/1950 | Field | 51/391 |
| 2,735,484 | 2/1956 | de Rossett | 132/76.4 |
| 2,746,461 | 5/1956 | Bocchino | 132/76.4 |
| 3,557,496 | 1/1971 | Martin | 51/394 |
| 3,640,031 | 2/1972 | Descant | 51/391 |
| 3,722,150 | 3/1973 | Pass | 51/391 |
| 3,956,858 | 5/1976 | Catlin et al. | 51/394 |
| 4,202,139 | 5/1980 | Hong et al. | 51/393 |
| 4,246,914 | 1/1981 | Keyser | 132/76.4 |
| 4,286,610 | 9/1981 | Jones et al. | 132/76.4 |
| 4,314,314 | 2/1982 | Friend | 51/393 |
| 4,343,910 | 8/1982 | Busch, Jr. et al. | 132/73 |
| 4,459,987 | 7/1984 | Pangburn | 128/355 |
| 4,537,207 | 8/1985 | Gilhaus | 132/76.4 |
| 4,541,443 | 9/1985 | Brothers et al. | 132/75.6 |
| 4,621,465 | 11/1986 | Pangburn | 51/392 |
| 4,688,356 | 8/1987 | Madzgalla | 51/391 |
| 4,712,552 | 12/1987 | Pangburn | 132/76.4 |

FOREIGN PATENT DOCUMENTS

| | | | |
|---|---|---|---|
| 0417177 | 9/1934 | United Kingdom | 51/407 |
| 0865060 | 4/1961 | United Kingdom | 132/76.4 |

*Primary Examiner*—John J. Wilson
*Assistant Examiner*—Frank A. LaViola
*Attorney, Agent, or Firm*—Dara Lynn Onofrio

[57] ABSTRACT

A strap of flexible material having abrasive material mounted on or embedded in the surface of a central portion thereof for use in the self-removal of foot calluses by persons who cannot or can only with difficulty bend over. The opposing ends of the strap do not have abrasive material mounted thereon and are gripped by the user with respective hands. Upon placing the abrasive material in contact with the foot callus, the user alternatingly pulls on one end of the strap with the left hand while providing tension with the right hand and then pulls on the other end of the strap with the right hand while providing tension with the left hand, in the manner of shining a shoe. As a result of this back and forth motion, the abrasive material rubs against the callus, thereby removing the surface layer of the callus through abrasion.

16 Claims, 1 Drawing Sheet

HAND-HELD FOOT CALLUS REMOVER

FIELD OF THE INVENTION

This invention relates generally to cosmetic abrasive devices and, in particular, concerns a hand-held device for abrading skin surfaces on the human foot which is useful in callus removal.

BACKGROUND OF THE INVENTION

It is well known to remove layers of calloused tissue using rigid abrading stones or other rigid devices. However, such rigid devices suffer from the disadvantage that they do not desirably conform to complexly curved skin contours, such as at the heel of the human foot.

Also, such rigid devices must be applied directly against the foot surface to be abraded by hand, which requires that the user be able to bend to the extent necessary to touch the sole of his or her foot. This is not always possible, especially for persons suffering from arthritis, back injury or other debilitating condition.

Although flexible abrasive sheets such as that disclosed in U.S. Pat. No. 4,459,987 can be used more effectively to abrade the surface of tissue at complexly curved skin contours, again the use of such hand-held sheets in foot callus removal requires that the user be sufficiently limber to reach the sole of his or her foot. Thus persons with arthritis or some other disability cannot conveniently use such flexible abrasive sheets to remove foot calluses.

SUMMARY OF THE INVENTION

The object of the invention is to overcome the aforementioned disadvantages of the prior art devices.

In particular, the object of the invention is to provide an abrasive device for use in removing calluses from feet which does not require that the user be able to touch the soles of his or her feet.

Another object of the invention is to provide a callus remover which can be used with little effort, particularly by older people with stiff joints or back injury, people crippled by arthritis or other debilitating disease and people with body shapes which prevent bending over.

A further object of the invention is to provide a device which can be used to stimulate blood circulation in the feet, remove dead callus growths and in general provide or promote greater health and comfort to the user's feet.

Yet another object of the invention is to provide a callus remover which is simple and inexpensive to manufacture.

The foregoing objects are realized by providing a strap of flexible material having abrasive material mounted on or embedded in the surface of a central portion thereof. The opposing ends of the strap do not have abrasive material mounted thereon and are gripped by the user with respective hands. Upon placing the abrasive material in contact with the foot callus, the user alternatingly pulls on one end of the strap with the left hand while providing tension with the right hand and then pulls on the other end of the strap with the right hand while providing tension with the left hand, in the manner of shining a shoe. As a result of this back and forth motion, the abrasive material rubs against the callus, thereby removing the surface layer of the callus through abrasion.

One advantage of the invention is that by increasing the length of the strap while still mounting the abrasive material in the central portion thereof, the extent to which the user must reach toward his or her feet is correspondingly reduced.

BRIEF DESCRIPTION OF THE DRAWINGS

The preferred embodiments of the invention will be described in detail hereinafter with reference to the drawings, wherein.

DETAILED DESCRIPTION OF THE PREFERRED EMBODIMENTS

Figure 1:
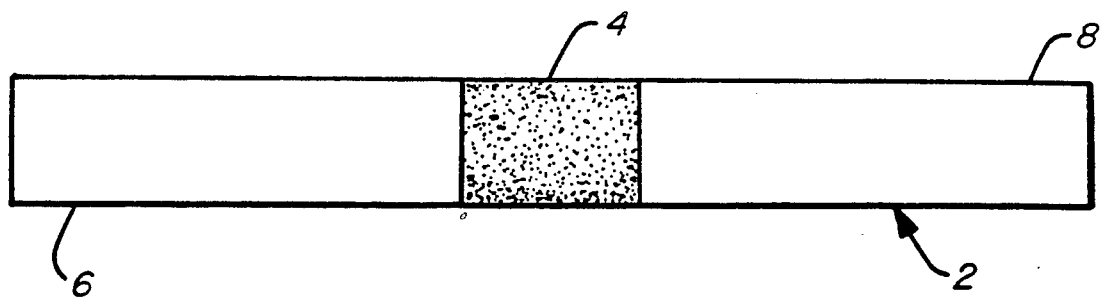
FIG. 1 is a top view of the callus remover in accordance with the preferred embodiments of the invention.

In accordance with both preferred embodiments of the invention as shown in FIG. 1, a unitary flexible sheet substrate 2 is provided in the form of a strap. In the first preferred embodiment, substrate 2 is made of cloth; in the second preferred embodiment, substrate 2 is made of silicone polymer. Other materials could be used provided that the end result is a flexible substrate of adequate strength to withstand the tension produced when the ends of the strap are pulled.

In both embodiments, an abrasive material 4 is mounted on one side of the strap in a central portion thereof. The portions of the strap extending from the edges of the central portion to the respective ends of the strap have no abrasive material applied thereon. The ends 6 and 8 of the strap are intended to be gripped in the respective hands of the user.

Although only one side of the strap need have an abrasive surface, it is possible to apply abrasive material to both sides of the central portion of the strap. For example, a coarse abrasive material can be applied on one side of the strap central portion and a fine abrasive material can be applied on the other side of the strap central portion. By providing abrasive materials of different roughness on opposing sides of the strap, the versatility of the callus remover in accordance with the invention is enhanced.

In accordance with the first preferred embodiment, the abrasive material 4 takes the form of a sheet of sandpaper which is adhered to the cloth substrate 2 by suitable means, for example, glue. As already mentioned, a second sheet of sandpaper having a roughness different than that of the first sheet of sandpaper can be adhered to the other side of the cloth substrate.

In accordance with the second preferred embodiment, the abrasive material 4 takes the form of protruding particulate matter which is embedded in one surface of the polymer substrate 2. The abrasive particulate consists of pumice or other fine abrasive suitable for abrading thickened areas of the skin. As shown in FIG. 1, the protruding particulate is embedded on at least one side of the central portion of the strap and is exposed to enable rubbing contact with the calloused skin. In the case where both sides of the strap have protruding particulate, the particles can be embedded on opposing surfaces of one sheet or on surfaces of respective sheets which are bonded together or bonded to opposing sides of a third sheet making up the substrate 2.

Figure 2:
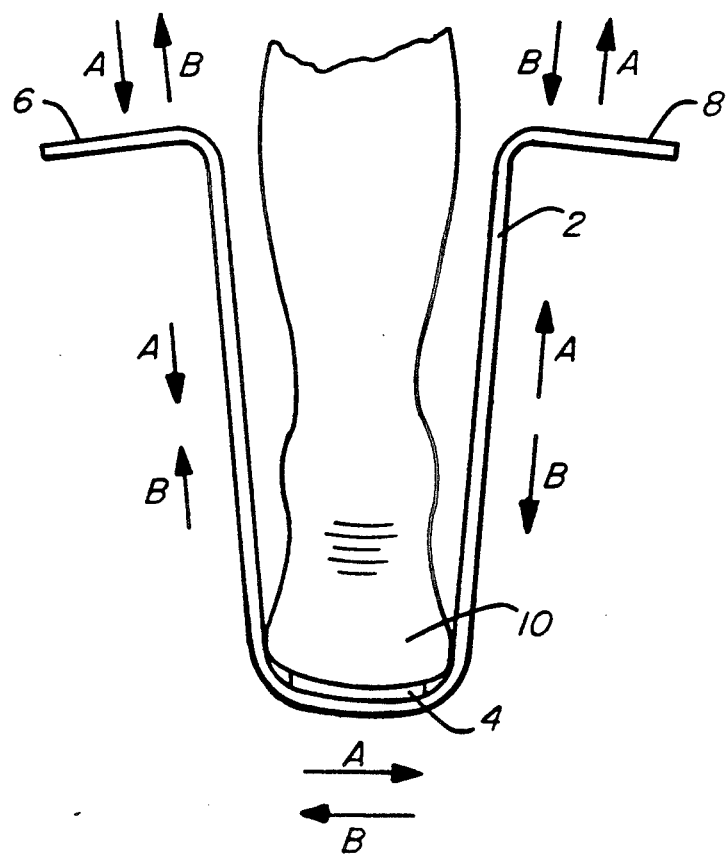
FIG. 2 is a side view of the callus remover in accordance with the first preferred embodiment of the invention, showing its position during foot callus removal.

FIG. 2 illustrates the manner in which the callus remover of the invention is manipulated by the user to remove calluses from the sole of the foot, in particular, the heel 10. The left end 6 of the strap is gripped in the left hand (not shown) of the user and the right end 8 of the strap is gripped in the right hand (not shown) of the user, with the abrasive material 4 in contact with the callus on the heel. By pulling harder on the left end 6 than on the right end 8, the user causes the various portions of the strap to move in the directions indicated by arrows B. As a result the abrasive material is moved to the left while in rubbing contact with the callus. Then by pulling harder on the right end 6 than on the left end 8, the user causes the various portions of the strap to move in the directions indicated by arrows A. As a result the abrasive material is moved to the right while in rubbing contact with the callus. These steps are repeated alternatingly, whereby the abrasive material rubs back and forth across the surface of the callus. Due to the tension being applied on both ends of the strap, the abrasive material is pressed against the callus during rubbing contact, so that the top layer of tissue is abraded. This abrading process is continued until the desired result has been achieved.

The aforementioned preferred embodiments have been disclosed for the purpose of illustration only and functionally equivalent variations and modifications could be made to those embodiments by a practitioner of ordinary skill in the art without departing from the scope of the claimed invention.

What is claimed is:

1. A hand-held device for abrading tissue from a sole of a human foot, the device having application for use by an infirmed or handicapped person, said device comprising:
    means for abrading tissue by rubbing contact with a surface of said tissue;
    means for supporting said abrading means, said supporting means having first and second ends;
    first means for applying a first tensile force to said first end of said supporting means; and
    second means for applying a second tensile force to said second end of said supporting means;
    wherein said supporting means, said first means and said second means comprise a unitary layer of flexible material;
    wherein said abrading means is arranged only on a substantially central portion of a surface of said unitary layer of flexible material; and
    further, wherein said unitary layer of flexible material is of sufficient length to permit a user, in a seated position to abrade the soles of his feet while remaining in a substantially upright position.

2. The hand-held device as defined in claim 1, wherein said supporting means comprises a substrate and said abrading means comprises sandpaper adhered to a surface of said substrate.

3. The hand-held device as defined in claim 2, wherein said substrate is made of cloth.

4. The hand-held device as defined in claim 1, wherein said supporting means comprises a substrate and said abrading means comprises protruding particulate matter embedded in a surface of said substrate.

5. The hand-held device as defined in claim 4, wherein said substrate is made of silicone polymer.

6. The hand-held device as defined in claim 1, wherein said unitary layer of flexible material has first and second surfaces, said abrading means being arranged on a substantially central portion of said first and second surfaces of said unitary layer of flexible material.

7. The hand-held device as defined in claim 6, wherein said abrading means comprises a layer of flexible material adhered to said unitary layer of flexible material, such that the flexible material conforms to contours of a skin surface.

8. The hand-held device as defined in claim 6, wherein said abrading means comprises protruding particulate matter embedded in said unitary layer of flexible material.

9. A hand-held device for abrading tissue from a sole of a human foot, the device having application for use by an infirmed or handicapped person, said device comprising:
    means for abrading tissue by rubbing contact with a surface of said tissue;
    means for supporting said abrading means, said supporting means having first and second ends;
    first extension means having an end connected to said first end of said supporting means; and
    second extension means having an end connected in said second end of said supporting means,
    wherein said supporting means, said first extension means and said second extension means comprise a unitary layer of flexible material wherein said abrading means is arranged only on a substantially central portion of a surface of said unitary layer of flexible material; and
    further, wherein said first and second extension means each have a sufficient length to permit a user, in a seated position to abrade the soles of his feet while remaining in a substantially upright position in the chair.

10. The hand-held device as defined in claim 9, wherein said supporting means comprises a substrate and said abrading means comprises sandpaper adhered to a surface of said substrate.

11. The hand-held device as defined in claim 10, wherein said substrate is made of cloth.

12. The hand-held deviced as defined in claim 9, wherein said supporting means comprises a substrate and said abrading means comprises protruding particulate matter embedded in a surface of said substrate.

13. The hand-held device as defined in claim 12, wherein said substrate is made of silicone polymer.

14. The hand-held device as defined in claim 9, wherein said unitary layer of flexible material has first and second surfaces, said abrading means being arranged on a substantially central portion of said first and second surfaces of said unitary layer of flexible material.

15. The hand-held device as defined in claim 14, wherein said abrading means comprises a layer of flexible material adhered-to said unitary layer of flexible material, such that the flexible material conforms to contours of a skin surface.

16. The hand-held device as defined in claim 14, wherein said abrading means comprises protruding particulate matter embedded in said unitary layer of flexible material.

* * * * *